US00PP21649P2

(12) United States Plant Patent
Heiser

(10) Patent No.: US PP21,649 P2
(45) Date of Patent: Jan. 18, 2011

(54) ***PETUNIA* PLANT NAMED 'BHTUN31501'**

(50) Latin Name: *Petunia×hybrida*
Varietal Denomination: BHTUN31501

(75) Inventor: Brian Heiser, Escondido, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/590,821

(22) Filed: Nov. 14, 2009

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent L Bell
(74) *Attorney, Agent, or Firm*—C. A. Whealy

(57) ABSTRACT

A new and distinct cultivar of *Petunia* plant named 'BHTUN31501', characterized by its upright and outwardly spreading to trailing plant habit; freely branching and vigorous growth habit; picotee-type flowers that are dark red purple in color with green-colored margins and dark violet-colored centers; and good garden performance.

1 Drawing Sheet

Botanical designation: *Petunia×hybrida.*
Cultivar denomination: 'BHTUN31501'.

BACKGROUND OF THE INVENTION

The present invention relates to a new and distinct cultivar of *Petunia* plant, botanically known as *Petunia×hybrida* and hereinafter referred to by the name 'BHTUN31501'.

The new *Petunia* plant is a product of a planned breeding program conducted by the Inventor in Bonsall, Calif. The objective of the breeding program is to create new *Petunia* plants with unique flower color combinations and good garden performance.

The new *Petunia* plant originated from a cross-pollination made by the Inventor on May 16, 2006 in Bonsall, Calif. of a proprietary seedling selection of *Petunia×hybrida* identified as code number PJ0559, not patented, as the female, or seed, parent with a proprietary seedling selection of *Petunia×hybrida* identified as code number PJ0528, not patented, as the male, or pollen, parent. The new *Petunia* plant was discovered and selected by the Inventor as a single flowering plant within the progeny of the stated cross-pollination in a controlled environment in Bonsall, Calif. on Jul. 17, 2007.

Asexual reproduction of the new *Petunia* plant by vegetative cuttings in a controlled greenhouse environment in Bonsall, Calif. since Jul. 20, 2007, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'BHTUN31501'. These characteristics in combination distinguish 'BHTUN31501' as a new and distinct cultivar of *Petunia:*

1. Upright and outwardly spreading to trailing plant habit.
2. Freely branching and vigorous growth habit.

3. Picotee-type flowers that are dark red purple in color with green-colored margins and dark violet-colored centers.
4. Good garden performance.

Plants of the new *Petunia* differ from plants of the female parent selection in the following characteristics:

1. Plants of the new *Petunia* are more spreading than and not as mounding as plants of the female parent selection.
2. Plants of the new *Petunia* have smaller flowers than plants of the female parent selection.

Plants of the new *Petunia* differ from plants of the male parent selection in the following characteristics:

1. Plants of the new *Petunia* are not as spreading as plants of the male parent selection.
2. Plants of the new *Petunia* have larger flowers than plants of the male parent selection.

Plants of the new *Petunia* can be compared to plants of 'Fortunia Burgundy Picotee', not patented. In side-by-side comparisons, plants of the new *Petunia* differed from plants of 'Fortunia Burgundy Picotee' primarily in flower color as plants of 'Fortunia Burgundy Picotee' had dark red purple-colored flowers with white-colored margins.

Plants of the new *Petunia* can also be compared to plants of 'Happy Gal', not patented. In side-by-side comparisons, plants of the new *Petunia* differed from plants of 'Happy Gal' primarily in flower color as plants of 'Happy Gal' had red purple-colored flowers with white-colored margins.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'BHTUN31501' grown in a container.

The photograph at the top of the sheet is a close-up view of typical flowers and leaves of 'BHTUN31501'.

DETAILED BOTANICAL DESCRIPTION

The aforementioned photographs and following observations, measurements and values describe plants grown in Bonsall, Calif., under commercial practice during the summer and early autumn in an outdoor nursery with day temperatures ranging from 18° C. to 38° C. and night temperatures ranging from 9° C. to 18° C. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'BHTUN31501'.

Parentage:

*Female, or seed, parent.*—Proprietary seedling selection of *Petunia×hybrida* identified as code number PJ0559, not patented.

*Male, or pollen, parent.*—Proprietary seedling selection of *Petunia×hybrida* identified as code number PJ0528, not patented.

Propagation:

*Type.*—Terminal vegetative cuttings.

*Time to produce a rooted young plant, summer.*—About 15 days at air temperatures of 29° C. and soil temperatures of 17° C.

*Time to produce a rooted young plant, winter.*—About 20 days at air temperatures of 21° C. and soil temperatures of 17° C.

*Root description.*—Medium in thickness, fibrous; white in color.

*Rooting habit.*—Freely branching; moderately dense.

Plant description:

*Plant and growth habit.*—Annual flowering plant; upright and outwardly spreading to trailing plant habit; vigorous growth habit; freely branching habit with about 14 lateral branches and numerous secondary and tertiary lateral branches per plant; pinching enhances development of lateral branches.

*Plant height.*—About 14 cm.

*Plant diameter* (*area of spread*).—About 57 cm.

*Lateral branches.*—Length: About 28 cm. Diameter: About 3 mm. Internode length: About 2.4 cm. Strength: Strong. Texture: Pubescent; viscid. Color: Close to 144A.

Foliage description:

*Arrangement.*—Alternate before flowering; opposite after flowers develop; simple.

*Length.*—About 6.6 cm.

*Width.*—About 3.6 cm.

*Shape.*—Elliptical.

*Apex.*—Broadly acute.

*Base.*—Attenuate.

*Margin.*—Entire.

*Texture, upper and lower surfaces.*—Pubescent; viscid.

*Venation pattern.*—Pinnate, arcuate.

*Color.*—Developing leaves, upper surface: Close to 137B. Developing leaves, lower surface: Close to 137C. Fully expanded leaves, upper surface: Close to 137B; venation, close to 144B. Fully expanded leaves, lower surface: Close to 147B; venation, close to 144B.

*Petioles.*—Length: About 1.4 cm. Diameter: About 4 mm. Texture, upper and lower surfaces: Pubescent. Color, upper and lower surfaces: Close to 146B.

Flower description:

*Flower type and habit.*—Single axillary salverform flowers; flowers face mostly upward or outward; freely flowering habit, about six to eight flower buds and open flowers per lateral branch.

*Natural flowering season.*—Long day responsive; long flowering period, plants flower from early spring until frost in the autumn, flowering continuous during this period; plants begin flowering about seven weeks after planting.

*Flower longevity on the plant.*—About four to five days; flowers persistent.

*Fragrance.*—Faint; sweet, floral.

*Flower size.*—Diameter: About 4.5 cm. Depth (height): About 4.7 cm. Tube length: About 2.7 cm. Throat diameter, distal end: About 1.4 cm. Tube diameter, proximal end: About 5 mm.

*Flower buds.*—Length: About 3.4 cm. Diameter: About 1 cm. Shape: Elongated oblong. Color: Towards the apex, close to 143A; towards the base, close to 79D.

*Petals.*—Quantity/arrangement: About five petals fused in a single whorl, funnelform. Petal lobe length (from throat): About 1.8 cm. Petal lobe width: About 2 cm. Petal lobe shape: Roughly obovate. Petal lobe apex: Acute with irregular shallow lobes. Petal lobe margin: Entire; sinuate. Petal lobe texture, upper surface: Smooth, glabrous; minute pubescence along margins. Petal lobe texture, lower surface: Pubescent. Throat texture: Smooth, glabrous. Tube texture: Pubescent. Color: When opening, upper surface: Centers, close to 72A; margins, close to 144A to 144B. When opening, lower surface: Centers, close to 79B; margins, close to 144A to 144B. Fully opened, upper surface: Centers, close to 72B; margins, close to 137A and 144B; venation, close to N79B. Fully opened, lower surface: Centers, close to 77B; margins, close to 138A and 144B; venation, close to N79B to N79C. Flower throat: Close to 83A; venation, close to N79A. Flower tube (outside): Close to 77A to 77B; venation, close to N79B.

*Sepals.*—Arrangement/appearance: Single whorl of five sepals fused at base, star-shaped calyx. Length: About 2.6 cm. Width: About 1 cm. Shape: Obovate. Apex: Rounded. Margin: Entire. Texture, upper and lower surfaces: Pubescent. Color, upper surface: Close to N137A. Color, lower surface: Close to 146B.

*Peduncles.*—Length: About 4.1 cm. Width: About 1.5 mm. Angle: About 45° from the stem axis. Strength: Moderately strong. Texture: Pubescent; viscid. Color: Close to 146B.

*Reproductive organs.*—Stamens: Quantity per flower: Five. Filament length: About 1.3 cm. Filament color: Close to 145D. Anther shape: Oval. Anther length: About 2 mm. Anther color: Close to 91A. Pollen amount: Moderate. Pollen color: Close to 97B. Pistils: Quantity per flower: One. Pistil length: About 1.5 cm. Style length: About 9 mm. Style color: Close to 145D. Stigma shape: Oval. Stigma color: Close to 201B. Ovary color: Close to 144A.

*Seed/fruit.*—Seed and/or fruit production has not been observed.

Pathogen/pest resistance: Plants of the new *Petunia* have not been noted to be resistant to pathogens or pests common to *Petunia*.

Garden performance: Plants of the new *Petunia* have been observed to have good garden performance and have been observed to tolerate rain, wind and temperatures ranging from about 0° C. to about 40° C.

It is claimed:

1. A new and distinct *Petunia* plant named 'BHTUN31501' as illustrated and described.

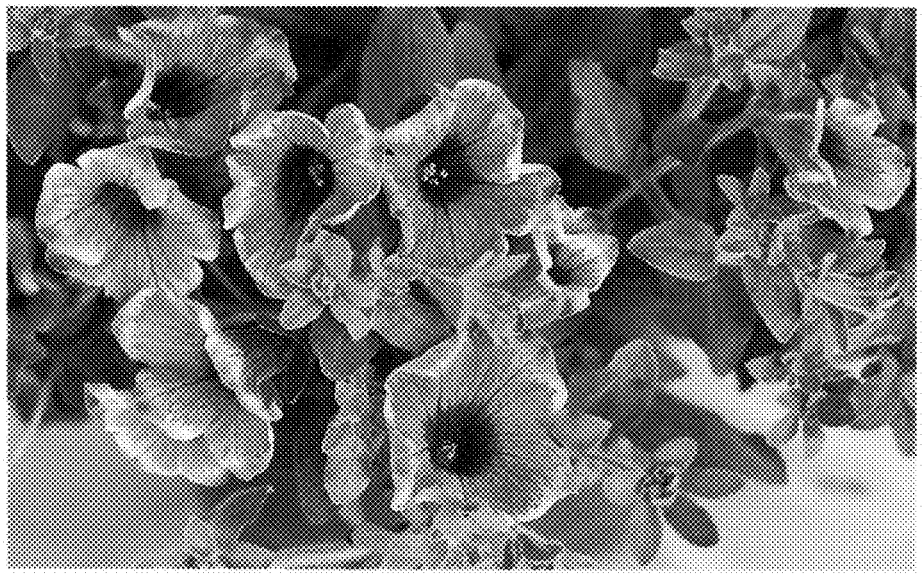
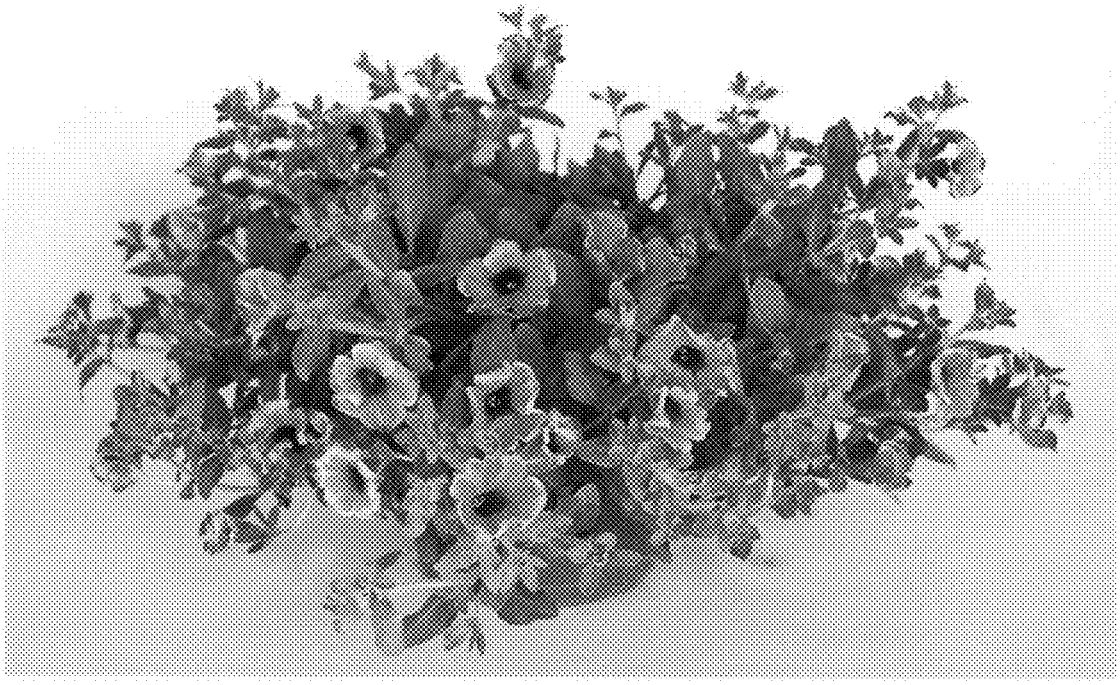

* * * * *